(12) United States Patent
Martir et al.

(10) Patent No.: US 11,190,732 B2
(45) Date of Patent: Nov. 30, 2021

(54) WORKSTATION FOR NEUROBIOLOGICAL DISORDER HEALTH PROFESSIONALS

(71) Applicant: Gama LLC, San Juan, PR (US)

(72) Inventors: Gabriel Jose Marcano Martir, Guaynabo, PR (US); Sheila Eileen Fridman Hurd, San Juan, PR (US)

( * ) Notice: Subject to any disclaimer, the term of this patent is extended or adjusted under 35 U.S.C. 154(b) by 0 days.

(21) Appl. No.: 16/412,483

(22) Filed: May 15, 2019

(65) Prior Publication Data

US 2020/0366867 A1   Nov. 19, 2020

(51) Int. Cl.

| | |
|---|---|
| *H04N 7/15* | (2006.01) |
| *G06N 20/00* | (2019.01) |
| *H04N 5/232* | (2006.01) |
| *G09B 5/06* | (2006.01) |
| *A61B 5/11* | (2006.01) |
| *A61B 5/00* | (2006.01) |
| *A61B 5/16* | (2006.01) |
| *G06Q 50/20* | (2012.01) |
| *H04R 1/10* | (2006.01) |

(52) U.S. Cl.
CPC ............ *H04N 7/152* (2013.01); *A61B 5/1113* (2013.01); *A61B 5/168* (2013.01); *A61B 5/4076* (2013.01); *G06N 20/00* (2019.01); *G09B 5/065* (2013.01); *H04N 5/23238* (2013.01); *H04N 7/155* (2013.01); *A61B 2503/06* (2013.01); *A61B 2505/07* (2013.01); *A61B 2505/09* (2013.01); *G06Q 50/2057* (2013.01); *H04R 1/1041* (2013.01); *H04R 2420/07* (2013.01)

(58) Field of Classification Search
CPC combination set(s) only.
See application file for complete search history.

(56) References Cited

U.S. PATENT DOCUMENTS

| | | | | |
|---|---|---|---|---|
| 6,321,912 | B1 * | 11/2001 | Lippert | ............... A45C 5/14 206/320 |
| 2001/0034615 | A1 * | 10/2001 | Wilkinson | ............ G06Q 50/22 705/2 |
| 2003/0023459 | A1 * | 1/2003 | Shipon | ............... G06F 19/3418 705/2 |
| 2004/0001137 | A1 * | 1/2004 | Cutler | ................. H04N 5/2259 348/14.08 |
| 2008/0266380 | A1 * | 10/2008 | Gorzynski | .............. H04N 7/15 348/14.08 |

(Continued)

*Primary Examiner* — Phung-Hoang J Nguyen
(74) *Attorney, Agent, or Firm* — Eugenio J. Torres-Oyola; Victoria M. Rodriguez-Reyes; Rafael Rodriguez-Muriel

(57) ABSTRACT

A workstation for neurobiological disorder health professionals that aids professionals tracking, evaluating and archiving clinical and educational progress through a web application using 360-degree video. The invention allows for organized communication between internal and external resources of an institution to tackle patient/student needs that merit immediate attention from specialists either in an individual or group setting. For additional expertise in acute cases, the institution can get access to consult with specialists around the world through the invention's directory of professionals. The invention allows clinical supervisors to train staff and ensure consistency in therapeutic interventions and evaluations, as well as supervisors in a school setting for consistency in educational programming. The invention also accelerates staff training time through targeted supervision.

17 Claims, 4 Drawing Sheets

(56) References Cited

U.S. PATENT DOCUMENTS

| | | | |
|---|---|---|---|
| 2010/0097441 A1* | 4/2010 | Trachtenberg | H04N 7/142 348/14.08 |
| 2011/0228921 A1* | 9/2011 | Singh | H04L 12/1831 379/202.01 |
| 2011/0228927 A1* | 9/2011 | Lee | H04L 9/0618 380/28 |
| 2016/0188799 A1* | 6/2016 | Borras | G06F 19/321 705/3 |
| 2017/0324572 A1* | 11/2017 | Biggs | H04L 12/18 |
| 2019/0086910 A1* | 3/2019 | Sarkar | G05B 23/0243 |

\* cited by examiner

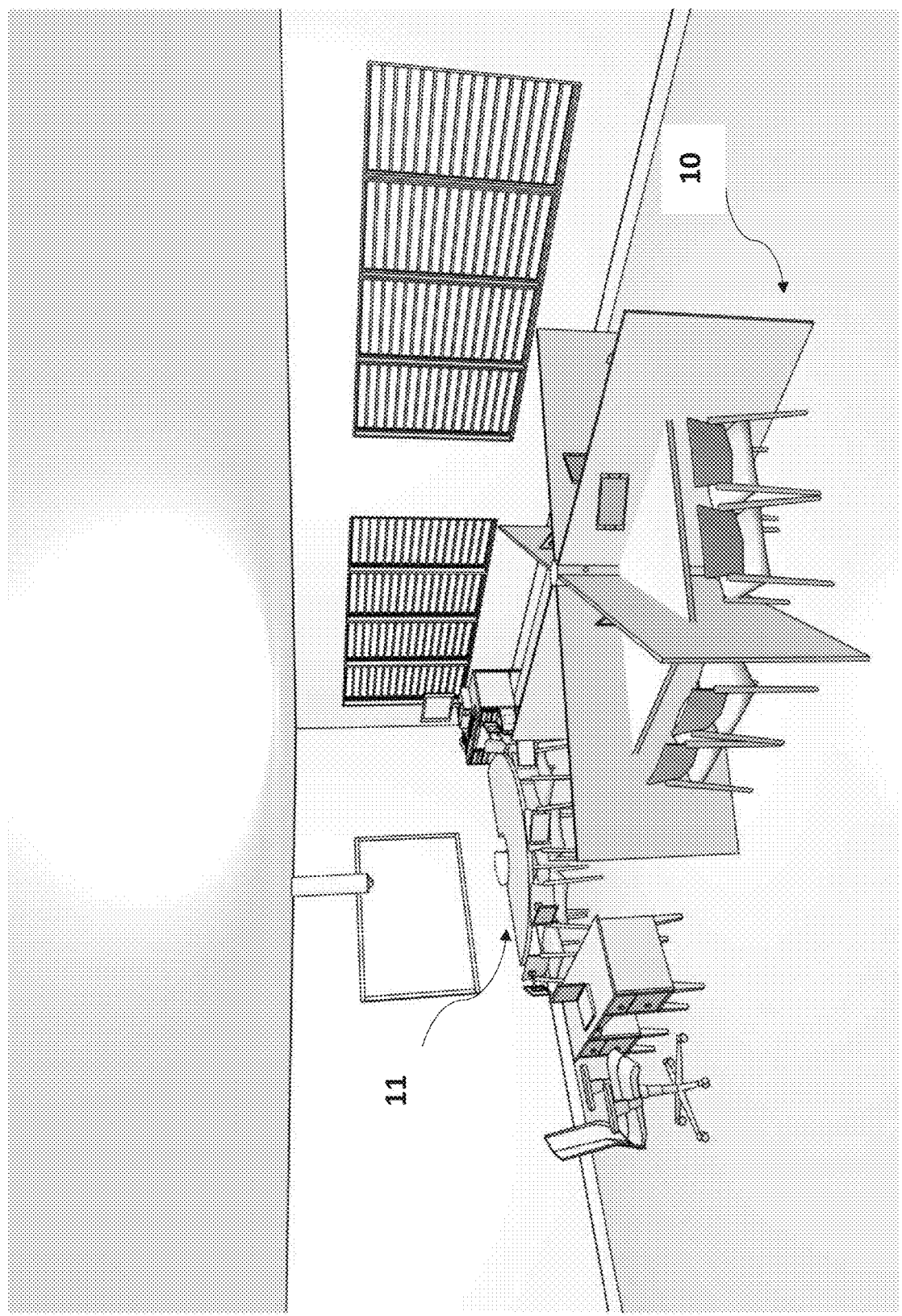

WORKSTATION FOR NEUROBIOLOGICAL DISORDER HEALTH PROFESSIONALS

FIELD OF INVENTION

The present disclosure relates to the field of special education to aid educators and clinical specialists when providing treatment to individuals with developmental, cognitive and/or neurological disorders such as Attention Deficit Disorder (ADD), Attention Deficit/Hyperactivity Disorder (ADHD), Autism Spectrum Disorder (ASD), Dyslexia and others. Specifically, the present disclosure is directed to a system and method for tracking, evaluating and archiving clinical and educational progress through a web application using video captured by an immersive camera. The present invention allows for communication between internal and external resources in an institution serving individuals with learning disabilities, helping to tackle patient/student needs that merit immediate attention from specialists. For additional expertise in acute cases, the institution has access to consult with specialists around the world through the platform's Directory of Professionals. The present invention allows clinical supervisors to train staff and ensure consistency in therapeutic interventions and evaluations, whether provided in the institution or home services, as well as supervisors in a school setting for consistency in educational programming. The present invention also accelerates staff training time through targeted supervision.

BACKGROUND OF THE INVENTION

Institutions that serve individuals with learning disabilities caused by developmental, cognitive and/or neurological disorders currently rely on the technology available to them, such as portable computers (laptops), tablet computers and video calling software (such as Skype™) to communicate "live" with external specialists in order to receive immediate feedback. This current practice is mostly used to aid educators in the implementation of behavior modification strategies for individuals with autism (ASD). To be able to fully capture the setting and all its parts, the laptop needs to be held by one staff member while another works with the individual. This approach requires a minimum of two people at a time on site, plus the attention of the external specialist. Other times, an educator would request another staff member to record them working with the individual to illustrate to the specialist a specific behavior when the specialist was not available via video call. Often the specialist had difficulties viewing the video due to the size of the media content and its slow data transfer rate. Due to limitations in video calling software, the video footage obtained during a call is not saved after viewing to use as reference. Stored or archived videos of live interactions to illustrate patient/student progress over time are difficult to generate and maintain due to the amount of personnel required, the amount of individuals that require interventions, and the unpredictability of the patient's behavior.

Furthermore, in some countries, like Puerto Rico, the demand for field specialists, similar to many rural areas of the United States, is very high and not enough specialists available for consultation, including Behavior Analysts and Speech and Language Pathologists. Any immediate need is not properly addressed due to specialist unavailability.

It is recommended that every individual that has one or more specialist in their multidisciplinary team work collaboratively to ensure academic and social-emotional progress. Every multidisciplinary team is comprised by different specialists, depending on the individual's educational and clinical needs, but most individuals who have severe learning disabilities caused by developmental, cognitive or neurological disorders have a minimum of three comprised by a Speech and Language, Speech and Language Pathologist, Behavior Analyst, Occupational Therapist, Psychologist and Physical Therapist, in addition to the Educational Specialist, and in acute cases, an educational or life coach is assigned for the safety and well-being of the individual.

It is important that clinical specialists observe their patients in the school and home settings, and they are needed to provide recommendations to staff and parents or legal guardians on a regular basis, especially for individuals who require significant support throughout their day. For example, it is a challenge for any specialist to visit a classroom without causing disruption since many students in a special education classroom have a very high sensitivity to distractions. Any change in the classroom setting will change the behavior of the student; thus, a specialist will not be able to observe a regular school activity because their presence disturbs the classroom setting. In addition, the specialist can visit the classroom at a certain time of day (scheduled time) and see none of the behaviors that need their recommendations, requiring another time to be scheduled or an effort by the educators to recreate the scenario and provoke the student to meltdown so that the specialist can witness the maladaptive behavior and the strategies used by the educator in order to provide new recommendations. In addition to classroom settings, the same type of issues may occur in rehabilitation centers, correctional facilities, and other institutions where treatment for individuals with similar disorders take place.

Most specialists work collaboratively with educators but due to time constraints and full case-loads, this communication has proven to be a challenge. Many of the communications have been traditionally in written format, and many of the difficulties in explaining a particular situation or challenging behavior in narrative form for the specialist to understand is often "lost in translation." Scheduling consultation time with specialists to provide this much needed feedback is also a challenge because of the specialists' availability, which often leads to inconsistencies, and in certain cases an immediate adjustment in the delivery of the instructional strategy is crucial to accomplish a modification, especially when this behavior is severe, such as cases that involve self-aggression or elopement.

The present invention aims to better serve a group of individuals with developmental, cognitive, and neurological disorders in a facility where specialists are scarce due to its geographical location and limited resources. The present invention is able to provide an immediate solution to institutions as it enables them to hire a virtual specialist such as a Board Certified Behavior Analyst (BCBA) to assess individuals, create treatment programs, monitor progress, supervise instruction, and provide immediate feedback to staff on their approach, thus providing a gain in employee performance through targeted supervision and training. The present invention allows for observations without causing a disruption in the environment, which is a known limitation in scenarios like Special Education. The present invention also allows for the multidisciplinary team (internal and external) to communicate and share important information requiring immediate attention or feedback. There are significant gains for individuals with disabilities and for the direct service and staff members by using the present invention, even more significant than having a specialist physically present.

Therefore, there is a need for a system and method for providing the assistance of specialists in both clinical and educational settings to observe, monitor, share, analyze and archive student/patient's progress.

SUMMARY OF THE INVENTION

The present invention overcomes the limitations of the prior art to provide assistance by field specialists to individuals with developmental, cognitive and/or neurological disorders that affect learning and communication. The disclosed invention allows for non-disruptive and non-distracting observations of a student or patient, while also providing tools for reviewing what was observed, aiding communication between all the professionals that are involved in an individual's treatment.

An object of the present invention is to allow a Behavior Analyst to observe and analyze a patient's behavior at home, clinic or school without being a distraction to said patient and changing his or her daily routine.

Another object of the present invention is to provide a platform for tagging and reviewing the video footage captured during a patient's treatment for better record-keeping of the patient's changes and responses to treatment.

A further object of the present invention is to provide educators and other professionals the ability to document specific behavior of a patient in order to allow fellow professionals to determine proper courses of action during treatment without the need to be physically with the patient.

The invention itself, both as to its configuration and its mode of operation will be best understood, and additional objects and advantages thereof will become apparent, by the following detailed description of a preferred embodiment taken in conjunction with the accompanying drawing.

The Applicant hereby asserts, that the disclosure of the present application may include more than one invention, and, in the event that there is more than one invention, that these inventions may be patentable and non-obvious one with respect to the other.

Further, the purpose of the accompanying abstract is to enable the U.S. Patent and Trademark Office and the general public, and especially the scientists, engineers, and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

BRIEF SUMMARY OF THE DRAWINGS

The accompanying drawings, which are incorporated herein, constitute part of the specifications and illustrate the preferred embodiment of the invention.

FIG. 4 shows a room comprising several embodiments of the present invention according to the teachings of the present disclosure.

DESCRIPTION OF THE PREFERRED EMBODIMENT

The present invention comprises of several hardware and software components that in combination provide the proper tools for specialists in the field of education and health servicing individuals with autism and other developmental, cognitive and neurological disorders. The education for individuals with mild to severe learning disabilities is complex and requires a multidisciplinary team to properly service their educational needs. This invention allows for both individual and group learning environments in various settings.

Individual Learning

Figure 1:
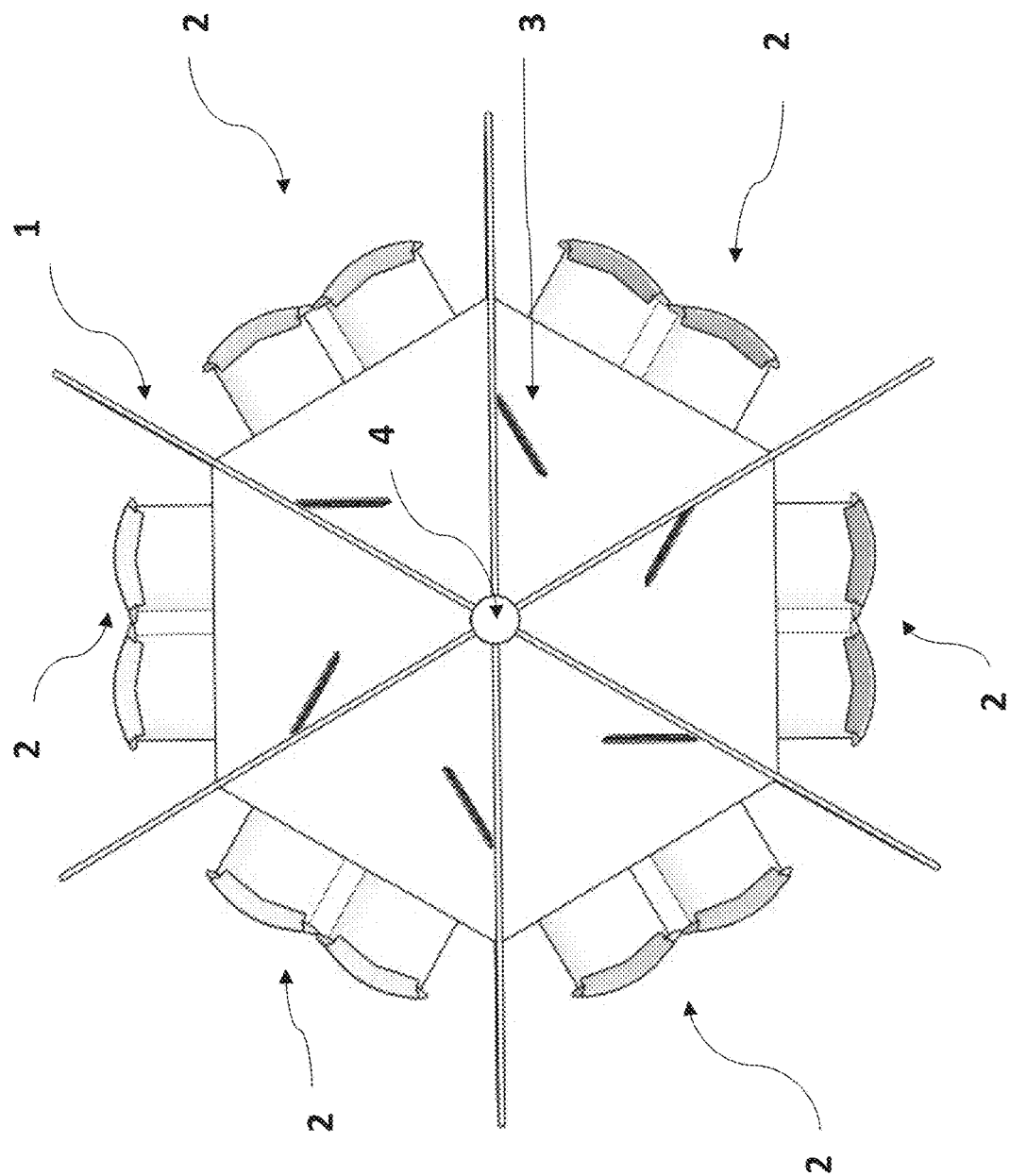
FIG. 1 shows the top view of an embodiment of the present invention directed at individual learning according to the teachings of the present disclosure.

As seen in FIG. 1, an exemplary embodiment of the present invention comprises a workstation module 1 that has four to six learning cubicles 2 that accommodate up to 2 seated individuals per cubicle. In some embodiments, each station has a computer 3 mounted, which runs a software platform for video calls, video recording and tagging. Some embodiments of the present invention may comprise wireless headsets for using during video calling sessions. The workstation module further comprises a circular tube in the middle holding an immersive (for example, 360-degree) camera 4, and an Internet access point. Said immersive camera 4 comprises 6 fisheye lenses with 6 unidirectional microphones. Said camera 4 stitches together the 6 images from said 6 fisheyes lenses in order to make one full image. The immersive camera 4 is used to have a full view of the room, which captures any movement and changes in the surrounding areas. Individuals being recorded can move in any direction of the room and the 360-degree viewing allows professionals to see where the patient goes and what stimulus they are drawn to.

Said immersive camera 4 and Internet access point are connected via ethernet cable to a network switch. The network switch is connected to a firewall that is connected to the public Internet network. The camera feed is streamed to a cloud computing system comprising one or more servers running a streaming engine software (SES). Said SES creates a live streaming feed and recording, which may be stored on a storage server. Data from said servers is accessed through a content delivery network that provides a globally-distributed network of proxy servers which cache content, such as web videos or other bulky media, more locally to consumers, thus improving access speed for downloading the content complying with regulation such as HIPAA. The present invention comprises a software platform stored on a secure web server which is accessed from the computer mounted on said workstation 1 and provides access to the stored patient data and video footage.

In some embodiments, the footage captured for each student is individually uploaded to the cloud computing system, where they will be stitched together as a 360-degree video. Both versions, the individual and the 360-degree, will be stored separately, allowing users to access video limited to only one student or for the complete group.

Group Learning

Figure 2:
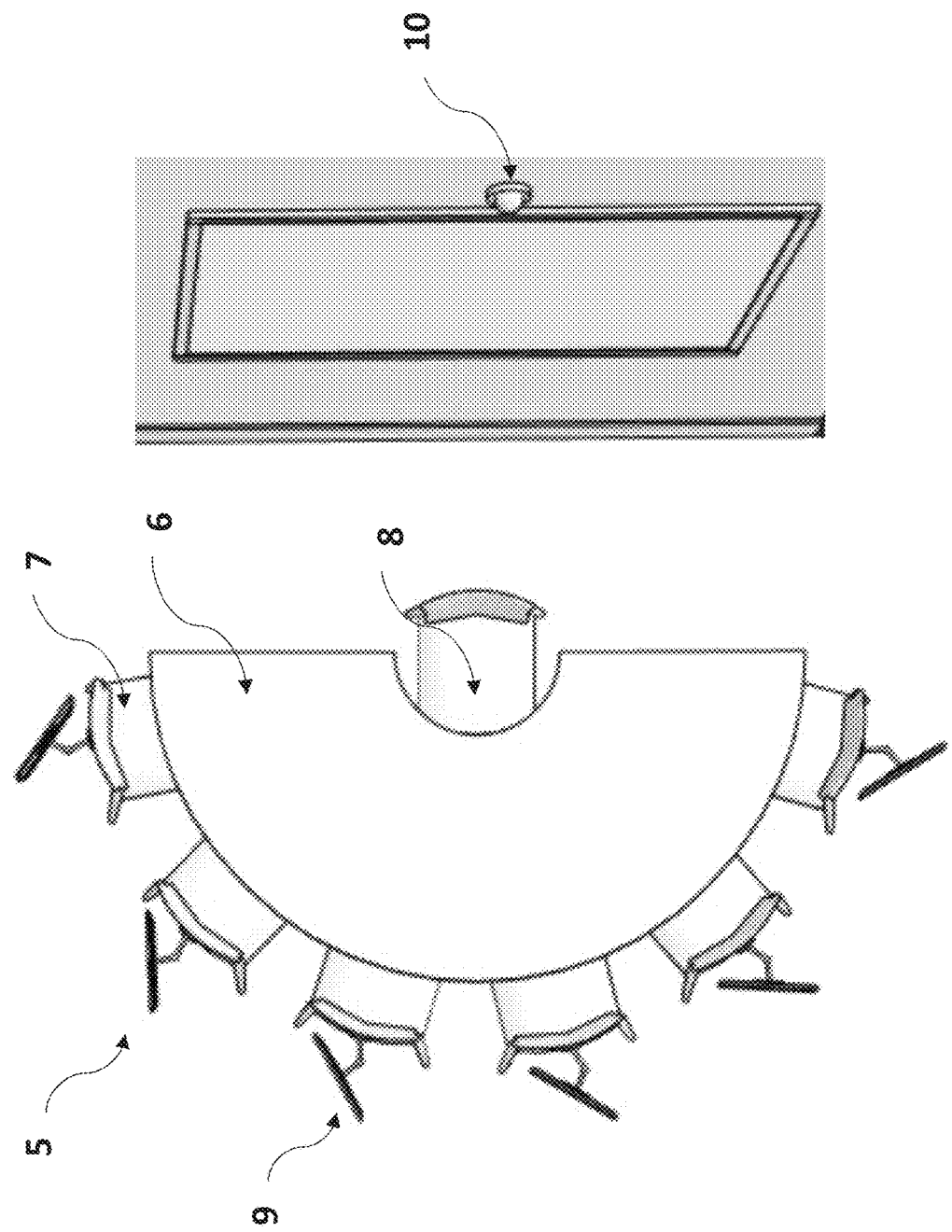
FIG. 2 shows the top view of an embodiment of the present invention directed at group learning according to the teachings of the present disclosure.

FIG. 2 shows another embodiment of the present invention, which comprises a group learning area 5. Said area 5 comprises an open space with a semicircular table 6 with six chairs 7 on the outside of the semi-circle and an open space 8 for one chair, which is meant for the instructor. Tablet computers 9 are moved from a cubicle learning station and mounted on the back of each patient's chair. The tablet computer's position facilitates individualized tagging and video chat. An immersive (for example, 180-degree) camera 10 is mounted from the rooftop or wall and positioned closer to the instructor in order to give a frontal viewing from the point of view of the instructor. Said camera 10 is connected via ethernet cable to a network switch. The network switch is connected to a firewall that is connected to the Internet network. The camera feed is streamed to a cloud computing system comprising one or more servers running a streaming engine software (SES). Said SES creates a live streaming feed and recording, which may be stored on a storage server. Data from said servers is accessed through a content delivery network that provides a globally-distributed network of proxy servers which cache content, such as web videos or other bulky media, more locally to consumers, thus improving access speed for downloading the content complying with regulation such as HIPAA. The present invention comprises a software platform stored on a secure web server which is accessed from the computer mounted on said workstation and provides access to the stored patient data and video footage.

Outside Learning and Home Instruction

The instructional staff, parent or specialist may take a camera-enabled mobile device, such as a tablet computer, everywhere they go for data collection purposes. Said tablet computers have an integrated camera that can be used for video recording and tagging outside the classroom when necessary.

Targeted Supervision (Software Component)

The present invention further comprises a software platform for accessing, tagging, and analyzing the live or recorded video footage acquired during classes or treatment sessions. Staff personnel from the treatment institution may log in to the software platform and select the work setting (home, school or clinic) and the patient with whom they will be working. This allows the platform to associate the tagging between the facilitator and the patient, and to determine which of the workstation's cubicles the camera should be recording. When tagging video, each tag makes a time stamp on the timeline of the video. Registered members may enter a "virtual observation room," comment on the tags that were made during the treatment session, and tag the professional related. These comments may be accessed by other staff members and specialists by logging into the platform as registered members.

Professionals may get notifications via email or in the app when they are requested to review a comment or timestamp in a video. Said notifications allow the professionals to go straight from the notification to the observation room (OR). On the OR the professional clicks on the tag made, observes the video, reads the comment on the tag and can give recommendations by adding their own comments. The professionals can also tag at any time from the OR. Staff members, prior to working with the same patient again must read the specialists' recommendations, which can include the implementation of strategies, make minor changes in the environment or continue the current strategy without changes. The immediate feedback of a specialist can help a patient's progress by immediately addressing an acute academic or social-emotional need in less than 24 hours. In conventional settings, it can take up to two weeks to get a specialist on site to observe and provide a consultation.

All comments and recommendations are referenced with the tag and video time stamp. The video player on the platform's OR allows for playback of 360-degree, 180-degree, and 2D formats. When the patient's information is entered, the learning cubicle is assigned so that the video player knows where he/she is sitting; when the video player moves from one degree to another, the information of the client automatically changes.

Live Supervision and Training

The web application has a "Live" function. The live function provides a video chat room. This functionality may be used for supervision purposes. The professional can choose between looking at the feed from any camera, including the tablet computer's 2D camera, the 360-degree camera in the workstation or the 180-degree camera one the group learning space. Many specialists are required to provide live supervision to staff members in order to be in compliance with regulatory agencies, especially when registering supervision hours for training purposes.

Further embodiments of the present invention may also comprise treatment recommendations using Machine Learning. All the tags from the captured footage may be stored in a separate server with comments and recommendations to be analyzed by Machine Learning software and help provide recommendations based on past actions and results. This allows the system to automatically provide a prompt with a suggested action when a behavior is detected.

Figure 3:
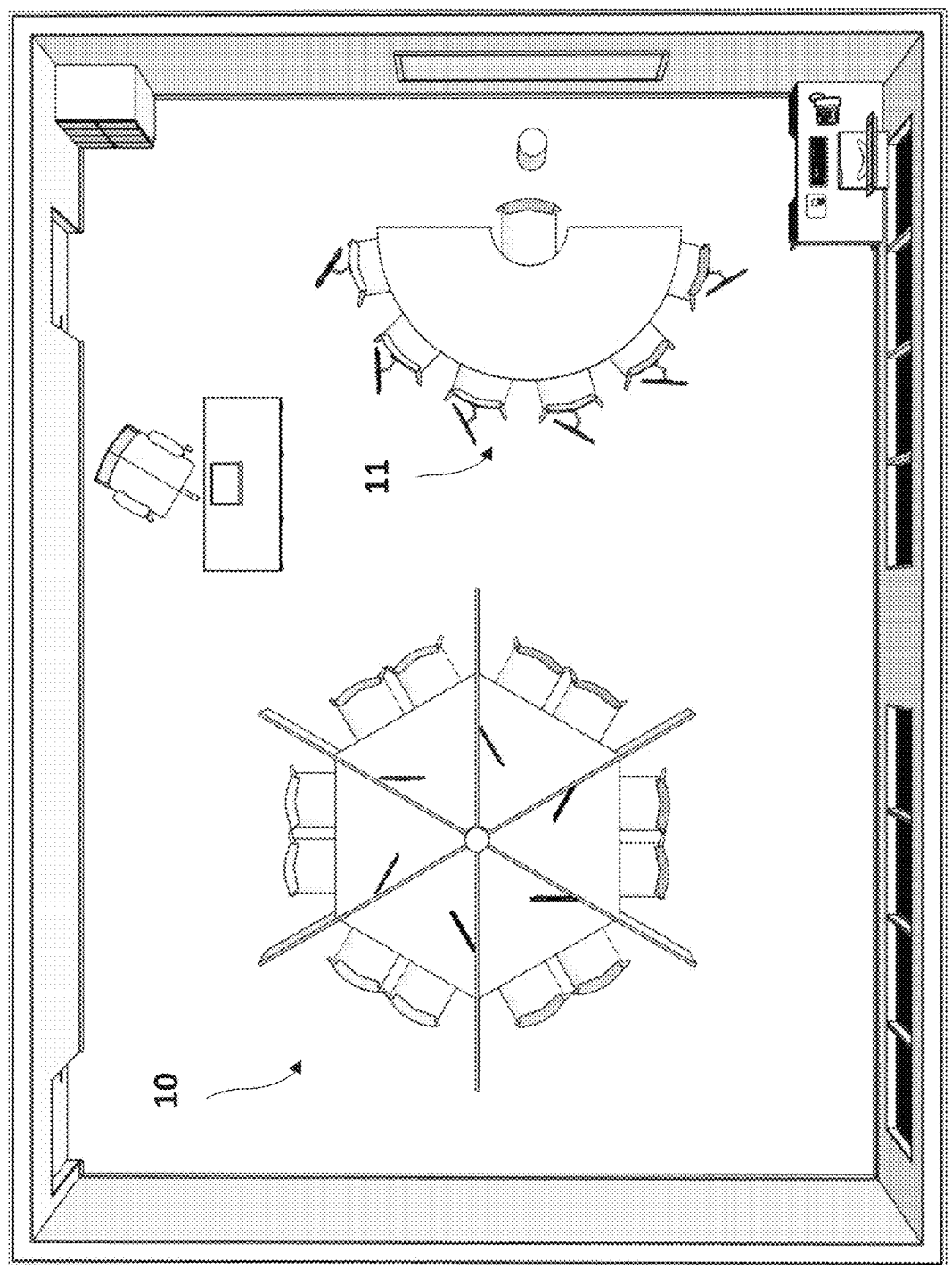
FIG. 3 shows a room comprising several embodiments of the present invention according to the teachings of the present disclosure.

As can be seen in FIGS. 3 and 4, several embodiments 11 and 12 of the present invention may be installed in the same room so that different types of treatment may be carried out either simultaneously with different patients or with the same patient throughout the day.

The software platform may further comprise a professionals directory, which provides classifications for specialized professionals available for consultation or ongoing care. The professionals assigned to a patient are registered and listed in the patient's profile inside the platform. Professionals will be listed when patient profile is set up.

Although certain exemplary embodiments and methods have been described in some detail, for clarity of understanding and by way of example, it will be apparent from the foregoing disclosure to those skilled in the art that variations, modifications, changes, and adaptations of such embodiments and methods may be made without departing from the true spirit and scope of the claims. Therefore, the above description should not be taken as limiting the scope of the invention which is defined by the appended claims The invention is not limited to the precise configuration described above. While the invention has been described as having a preferred design, it is understood that many changes, modifications, variations and other uses and applications of the subject invention will, however, become apparent to those skilled in the art without materially departing from the novel teachings and advantages of this invention after considering this specification together with the accompanying drawings. Accordingly, all such changes, modifications, variations and other uses and applications which do not depart from the spirit and scope of the invention are deemed to be covered by this invention as defined in the following claims and their legal equivalents. In the claims, means plus function clauses, if any, are intended to cover the structures described herein as performing the recited function and not only structural equivalents but also equivalent structures.

All of the patents, patent applications, and publications recited herein, and in the Declaration attached hereto, if any, are hereby incorporated by reference as if set forth in their entirety herein. All, or substantially all, the components disclosed in such patents may be used in the embodiments of the present invention, as well as equivalents thereof. The details in the patents, patent applications, and publications incorporated by reference herein may be considered to be incorporable at applicant's option, into the claims during prosecution as further limitations in the claims to patently distinguish any amended claims from any applied prior art.

What is claimed:

1. A workstation for educators and clinical professionals, comprising:
   a workspace module comprising a plurality of cubicles;
   a tube located in the middle of said workspace module comprising an immersive camera;
   an Internet access point;
   a plurality of computers;
   wherein each computer of said plurality of computers is connected to a secure cloud server comprising:
      at least one processor;
      a storage module;
      a memory module;
      a video capturing module; and
      program instructions stored on said storage module for execution by said processor, said stored program instructions comprising:
         program instructions for making video calls;
         program instructions for recording video;
         program instructions for recording video calls;
         program instructions for tagging video;
         program instructions for creating at least one user profile;
         program instructions for associating recorded video with said at least one user profile;
         program instructions for associating said immersive camera to at least one of said plurality of cubicles;
   wherein tagging video comprises adding a plurality of tags to said video in a live manner while a video call or video recording is in progress, and said plurality of tags is directed at providing information related to the video and unrelated to structuring data;
   wherein said secure cloud server further comprises a machine learning software module configured to collect video tag and patient or student data, extract and analyze comments and recommendations from the video tag and patient or student data, and provide treatment recommendations based on said video tag and patient or student data;
   wherein the recorded video is individually uploaded to the cloud server and stitched together as a 360-degree video; and
   wherein both the individually uploaded recorded video and the 360-degree video are stored separately, allowing a user to access video for either one patient/student or for a complete group of patients/students.

2. The workstation of claim 1, wherein said immersive camera is a 360-degree camera.

3. The workstation of claim 1, wherein said plurality of computers comprises desktop computers, laptop computers, or tablet computers.

4. The workstation of claim 1, further comprising a wireless headset.

5. The workstation of claim 1, wherein said software module is further configured to stream live video.

6. The workstation of claim 1, wherein said secure web server further comprises a professionals directory software module.

7. A workstation for educators and clinical professionals, comprising:
   a workspace module comprising a semicircular table;
   a plurality of chairs;
   an immersive camera configured to capture the front view of said workspace module;
   an Internet access point;
   a plurality of computers mounted of the back of said plurality of chairs;
   wherein each computer of said plurality of computers is connected to a secure cloud server comprising:
      at least one processor;
      a storage module;
      a memory module;
      a video capturing module; and
      program instructions stored on said storage module for execution by said processor, said stored program instructions comprising:
         program instructions for making video calls;
         program instructions for recording video;
         program instructions for recording video calls;
         program instructions for tagging video;
         program instructions for creating at least one user profile;
         program instructions for associating recorded video with said at least one user profile;
         program instructions for associating said immersive camera to at least one of said plurality of cubicles;
   wherein tagging video comprises adding a plurality of tags to said video in a live manner while a video call or video recording is in progress, and said plurality of tags is directed at providing information related to the video and unrelated to structuring data;
   wherein said secure cloud server further comprises a machine learning software module configured to collect video tag and patient or student data, extract and analyze comments and recommendations from the video tag and patient or student data, and provide treatment recommendations based on said video tag and patient or student data;
   wherein the recorded video is individually uploaded to the cloud server and stitched together as a 360-degree video; and
   wherein both the individually uploaded recorded video and the 360-degree video are stored separately, allowing a user to access video for either one patient/student or for a complete group of patients/students.

8. The workstation of claim 7, wherein said immersive camera is a 360-degree camera.

9. The workstation of claim 7, wherein said immersive camera is a 180-degree camera.

10. The workstation of claim 7, wherein said plurality of computers comprises desktop computers, laptop computers, or tablet computers.

11. The workstation of claim 7, further comprising a wireless headset.

12. The workstation of claim 7, wherein said secure web server further comprises a professionals directory software module.

13. A method for monitoring treatment patients with developmental, cognitive and/or neurological disorders, comprising the steps of;
   configuring an immersive camera to detect at least one patient in a workstation;
   recording video of a treatment session using said immersive camera;
   storing said video on a secure web server, wherein said secure web server comprises a software application configured to allow tagging said video;
   tagging said video with comments related to said patient;
   creating at least one user profile;
   associating recorded video with said at least one user profile;

associating said immersive camera to said at least one patient;

wherein tagging video comprises adding a plurality of tags to said video in a live manner while video recording is in progress, and said plurality of tags is directed at providing information related to the video and unrelated to structuring data;

wherein said secure cloud server further comprises a machine learning software module configured to collect video tag and patient or student data, extract and analyze comments and recommendations from the video tag and patient or student data, and provide treatment recommendations based on said video tag and patient or student data;

wherein the recorded video is individually uploaded to the cloud server and stitched together as a 360-degree video; and wherein both the individually uploaded recorded video and the 360-degree video are stored separately, allowing a user to access video for either one patient/student or for a complete group of patients/students.

14. The method of claim 13, wherein said workstation comprises a plurality of individual treatment cubicles.

15. The method of claim 13, wherein said workstation comprises a group learning semicircular table.

16. The method of claim 13, wherein said immersive camera is a 360-degree camera.

17. The method of claim 13, wherein said immersive camera is a 180-degree camera.

* * * * *